United States Patent
Dosoretz et al.

[11] Patent Number: 6,010,665
[45] Date of Patent: Jan. 4, 2000

[54] MULTI-WAVELENGTH BASED OZONE MEASUREMENT METHOD AND APPARATUS

[75] Inventors: Victor J. Dosoretz; Baruch Mazor, both of Newton Center; Scott Keller, Lincoln; Daniel Behr, Needham, all of Mass.

[73] Assignee: IN USA, Inc., Needham, Mass.

[21] Appl. No.: 08/953,157

[22] Filed: Oct. 17, 1997

Related U.S. Application Data

[60] Provisional application No. 60/028,723, Oct. 18, 1996.

[51] Int. Cl.[7] .................................................. G01N 21/29
[52] U.S. Cl. ..................................... 422/82.05; 422/82.09; 422/82.11; 356/320; 250/339.05; 250/339.13; 250/343
[58] Field of Search ............................ 422/82.05, 82.09, 422/82.06, 82.11; 436/135; 356/319.32, 326, 328; 250/339.05, 343, 339.13

[56] References Cited

U.S. PATENT DOCUMENTS

| | | | |
|---|---|---|---|
| 3,727,050 | 4/1973 | Kerr | 250/43.5 |
| 3,761,724 | 9/1973 | Dennis | 250/565 |
| 3,843,258 | 10/1974 | Shupe | 356/88 |
| 3,916,195 | 10/1975 | Burch et al. | 250/345 |
| 3,925,667 | 12/1975 | Staab | 250/343 |
| 3,937,962 | 2/1976 | Faulhaber et al. | 250/346 |
| 3,970,387 | 7/1976 | Faulhaber et al. | 356/51 |
| 4,061,918 | 12/1977 | Preier et al. | 250/343 |
| 4,126,396 | 11/1978 | Hartmann et al. | 356/434 |
| 4,156,143 | 5/1979 | Adrian | 250/345 |
| 4,156,812 | 5/1979 | Staab | 250/345 |
| 4,180,732 | 12/1979 | Fabinski et al. | 250/344 |
| 4,281,248 | 7/1981 | Fabinski et al. | 250/345 |
| 4,426,640 | 1/1984 | Becconsall et al. | 340/632 |
| 4,500,207 | 2/1985 | Maiden | 356/409 |
| 4,525,069 | 6/1985 | Tanaka et al. | 356/435 |
| 4,557,603 | 12/1985 | Oehler et al. | 356/418 |
| 4,560,875 | 12/1985 | Crowder | 250/343 |
| 4,567,366 | 1/1986 | Shinohara | 250/339 |
| 4,676,642 | 6/1987 | French | 356/346 |
| 4,718,762 | 1/1988 | Wiget et al. | 356/319 |

(List continued on next page.)

*Primary Examiner*—David A. Redding
*Attorney, Agent, or Firm*—Weingarten, Schurgin, Gagnebin & Hayes LLP

[57] ABSTRACT

Systems and methods for providing an ultra-stable measurement of the density of a fluid/gas species such as ozone in a mixture. The technique is based on information extracted from multi-wavelength light absorption, at which the species exhibits different absorption properties (coefficient values). The technique provides real-time compensation for short- and long-term instability in the light source and detector, and for detectable changes in the optical characteristics of the cell, thus improving the accuracy of the measurement while making frequent zeroing of the instrument unnecessary. In addition, the invention provides a high-performance technique for measuring ultra-high ozone densities using absorption at the Chappuis band.

The invention provides in an embodiment a system and method for detection of a gas component such as ozone in a gas mixture utilizing a light source providing light output in the visible spectrum corresponding to maximum and minimum absorption wavelengths for the gas component of interest. A process gas containing ozone or other gas component to be measured is supplied to a cell or cuvette having an optical input end and an optical output end. The light sources are desirably coupled to a first ("sample") optical path which provides light from the sources to the optical input end of the cell, and to a second ("reference") optical path which does not pass through the sample gas. A sensor apparatus is disposed to receive the light transmitted through the cell, and through the second optical path. The second optical path serves as a reference path, while the first optical path serves as a measurement path. The sensor apparatus provides electrical outputs representative of the intensity of light impinging thereon, the outputs being provided to a processor operative to calculate the concentration of the ozone or other gas component of interest in the gas cell.

16 Claims, 3 Drawing Sheets

U.S. PATENT DOCUMENTS

| | | | |
|---|---|---|---|
| 4,941,747 | 7/1990 | Dakin | 356/346 |
| 5,040,895 | 8/1991 | Laurent et al. | 356/346 |
| 5,146,283 | 9/1992 | Parnoff et al. | 356/246 |
| 5,173,749 | 12/1992 | Tell et al. | 356/437 |
| 5,222,389 | 6/1993 | Wong | 73/31.02 |
| 5,223,715 | 6/1993 | Taylor | 250/343 |
| 5,294,796 | 3/1994 | Fee et al. | 250/338.5 |
| 5,298,751 | 3/1994 | Fee et al. | 250/338.5 |
| 5,396,328 | 3/1995 | Jestel et al. | 356/358 |

MULTI-WAVELENGTH BASED OZONE MEASUREMENT METHOD AND APPARATUS

CROSS REFERENCE TO RELATED APPLICATIONS

This application claims the benefit of U.S. Provisional Application Ser. No. 60/028,723, filed Oct. 18, 1996, the entire disclosure of which is incorporated herein by reference.

STATEMENT REGARDING FEDERALLY SPONSORED RESEARCH OR DEVELOPMENT n/a

BACKGROUND OF THE INVENTION

Ozone gas exhibits various absorption bands in the UV, visible and infrared spectra. The most prominent absorption band occurs in the UV range around 254 nm, the Hartley band. This band has long been used in absorption spectrophotometers for ozone measurement, and UV absorption has become a common, proven analytical method to determine ozone concentrations. UV absorption is also recognized by many international entities (such as IOA, EPA and NIST) as the Standard Method for measuring gas-phase ozone.

The use of UV absorption photometry for ozone measurement derives from a number of factors. The strong absorption at 254 nm lends to instruments with small-geometry and very wide dynamic range. In addition, reliable light sources that produce the desired discrete spectrum are readily available in the form of low pressure mercury vapor lamps.

Beer-Lambert Absorption Equation

The mathematical relationship between light absorption and gas density can be described by the following generalized equation:

$$I = \int_{\lambda_l}^{\lambda_h} I_0(\lambda) e^{-\varepsilon(\lambda) \ast L \ast C} d\lambda \qquad (1)$$

where I is the integrated radiant power through the sample, $(\lambda_h - \lambda_l)$ is the measurement spectral bandwidth, $I_0(\lambda)$ is the power spectrum measured at zero gas density, $\varepsilon(\lambda)$ is the absorption coefficient spectrum, L is the length of the optical path, and C is the ozone density in mass/volume. In practice, when the absorption coefficient is assumed to be constant within the measurement band or when the bandwidth is sufficiently narrow (approximating a single wavelength or monochromatic condition), the standard Beer-Lambert equations are used as follows:

$$I = I_0 \times e^{-\varepsilon \ast L \ast C} \qquad (2)$$

or $$C = \frac{\ln\left(\frac{I_0}{I}\right)}{\varepsilon \times L} \qquad (3)$$

Typically, absorption photometers are designed to use equation (3) under the assumptions that $\varepsilon$ and L are known constants and that I and $I_0$ can be accurately measured. Once those assumptions are satisfied, the instrument calculates C as a linear function of the absorbance $\ln(I_0/I)$. Key issues which can lead to deviations from these basic assumptions and produce inaccurate measurements are discussed below.

Measurement of $I_0$ and I $I_0$ represents the radiant power through the sample optical path with ozone free sample (zero density). The frequency at which $I_0$ needs to be measured (frequency at which the instrument needs to be zeroed) depends on the stability of the optical system. I, the radiant power through the sample, represents the real-time signal in the presence of ozone in the cuvette.

In practical systems, the measurements will always include "noise" components that affect the accuracy of the estimated signals, and in turn the accuracy of the calculated ozone density. The "noise" level is typically constant and independent of gas density, while the signal level decreases exponentially with density. Therefore, at ultra-high densities, the signal-to-noise ratio drops exponentially, and correspondingly, the error in the calculated density increases rapidly. To alleviate this problem and attain high signal-to-noise ratio at the upper end of the instrument's range, it is essential to maintain high signal level at ultra-high densities.

Instability of the light source and detector, and changes in the optical characteristics of the cuvette due to for example soil buildup, solarization, etc., are other issues affecting the accuracy of the estimated signal. To compensate for these problems, it is essential to measure $I_0$ very frequently.

Optical Path and Ultra-high Densities

Equations (1) through (3) assume a linear optical path of a predetermined length L. The linear requirement implies same optical path length for all light rays interacting with the absorbing species. The length of the optical path is a design parameter determined by tradeoffs among the specific absorption coefficients, the targeted ozone density range, the minimum signal-to-noise ratio (or precision and linearity at the upper end of the range), and the tolerance for zero drifts. Typically, the higher the density range, the higher the minimum signal-to-noise ratio, and the larger the absorption coefficient, a shorter optical path lengths and more stringent manufacturing tolerances are required. In addition, a short path length typically implies a tighter restriction for gas flow which presents a challenge if high flow rates are required. To address this issue and to optimize the above tradeoffs while delivering high precision performance, it is necessary to use spectra in which the targeted species exhibit lower absorption values.

High Density High Pressure Needs

Industrial applications of ozone now require very high ozone densities, in excess of ~300 g/Nm$^3$. Generator manufacturers are in fact meeting this demand with newly designed generators capable of delivering these ozone levels. In addition, many industrial applications require that ozone be delivered and measured at high pressures. All other factors being constant, the ozone density C, is a function of the pressure of the sample gas. Since compressed ozone typically behaves as an ideal gas, increasing the pressure by a factor of $\alpha$, would result in a measured density $C_P$ equal to $(\alpha \times C)$. For example, in bleaching paper pulp applications, the output of an ozone generator, typically $\approx 100$ g/Nm$^3$, is compressed to several atmospheres before it can successfully be used in a modified Kraft sequence. The ozone density of this compressed sample, $C_P$, is therefore several hundred g/m$^3$.

The Chappuis Band

As explained before, the length of the optical path is determined by tradeoffs among the absorption coefficient, the targeted ozone density range, the budgeted minimum signal-to-noise ratio, and the tolerance for zero drifts. When the targeted density is ultra high, these tradeoffs may result in impractical geometry for the cell or/and inadequate analyzer performance, for absorption in the Hartley band. In this case, an alternative approach is to operate the spectrophotometer at the ozone absorption peak in the Chappuis band around 604 nm.

The absorption coefficient at the Chappuis band peak is $\epsilon=0.055$ cm$^{-1}$ (for comparison, the absorption coefficient at 254 nm is 134.0 cm$^{-1}$). This small value of $\epsilon$ leads to more practical gap/cell geometry. However, in order to measure ultra-high ozone density at a performance comparable to UV-based instruments requires extremely stable signals ($I_0$ and I), high signal-to-noise figures, and very small zero drifts.

BRIEF SUMMARY OF THE INVENTION

The invention provides an ultra-stable technique for measuring the density of a fluid/gas species in a mixture. The technique is based on information extracted from multi-wavelength light absorption, at which the species exhibit different absorption properties (coefficient values). This novel technique provides real-time compensation for short- and long-term instability in the light source and detector, and for detectable changes in the optical characteristics of the cell, thus improving the accuracy of the measurement while making frequent zeroing of the instrument unnecessary. In addition, specifically for ozone, this invention provides a high-performance technique for measuring ultra-high ozone densities using absorption at the Chappuis band.

BRIEF DESCRIPTION OF THE SEVERAL VIEWS OF THE DRAWING

The system and method disclosed herein will be more fully understood by referring to the detailed description, in conjunction with the appended drawings, of which.

DETAILED DESCRIPTION OF THE INVENTION

Figure 1:
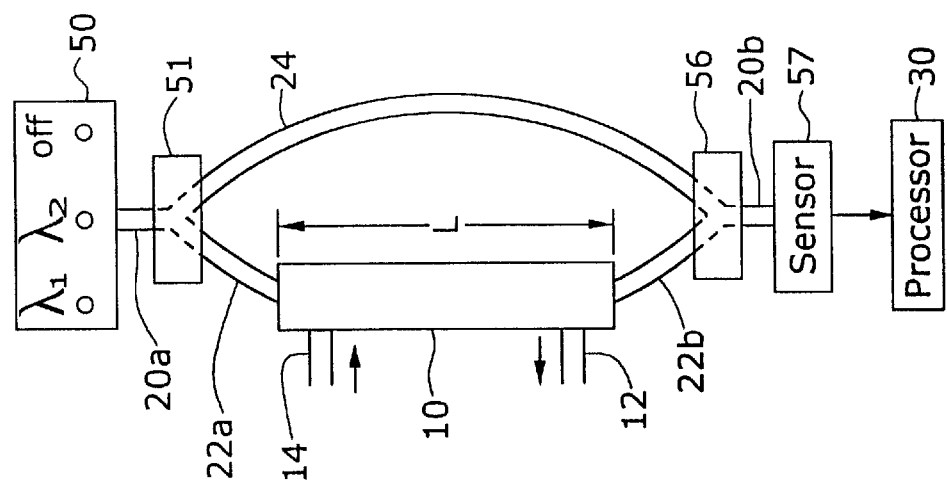
FIG. 1 depicts a dual wavelength measurement apparatus in accordance with a particularly advantageous embodiment of the invention.

FIG. 1 schematically illustrates a particularly advantageous embodiment which comprises a flow-through cell or cuvette 10 of a pathlength L, having a gas inlet port 14 and a gas outlet port 12. A light source 50 comprising an electronically controlled multi-wavelength light source (for the ozone application, and in this embodiment, the source can produce light at wavelength $\lambda_1$=604 nm; or $\lambda_2$=850 nm; or no light (dark)) coupled to a two-way optical splitter 51 by light guide 20a which in turn provides a light guide branch 22a to the optical input end of cell 10, and a second branch 24. The optical output end of cell 10 has connecting light guide branch 22b, which, with second branch 24 feeds into electronically controlled two-way optical switch 56. The output of switch 56 is connected to sensor apparatus 57, which sends electrical output to processor 30. The light guide may be an optical fiber or other light pipe for providing defined optical paths to guide the light from the light source 50 to its destination(s). The path through cell 10 serves as a measurement path, and the path 24 to sensor apparatus 57 serves as a reference path. Light source 50 could alternately comprise dual light emitting devices 16 and 18 for emitting at the respective desired wavelengths. Similarly, sensor apparatus 57 could also alternately comprise dual photosensors 26 and 28, for receiving the sample and reference inputs (as is seen in, e.g., FIG. 2.)

In operation of this embodiment, the light radiant signals measured and used in the calculations are as follows:

|  | $t = t_0$ Zero Gas Density | | $t = t_1$ Measured Gas Density | |
| --- | --- | --- | --- | --- |
|  | $\lambda_1$ | $\lambda_2$ | $\lambda_1$ | $\lambda_2$ |
| Cuvette | $I_{0c1}$ | $I_{0c2}$ | $I_{1c1}$ | $I_{1c2}$ |
| Reference | $I_{0r1}$ | $I_{0r2}$ | $I_{1r1}$ | $I_{1r2}$ | where $I_{0c1}$ is the radiant signal at zero gas density, measured through the cuvette at wavelength $\lambda_1$;

$I_{0r1}$ is the radiant signal, measured through the reference path, at wavelength $\lambda_1$;

$I_{0c2}$ is the radiant signal at zero gas density, measured through the cuvette at wavelength $\lambda_2$;

$I_{0r2}$ is the radiant signal, at zero time measured through the reference path, at wavelength $\lambda_2$;

$I_{0D}$ is the signal at zero gas density, with the light source off;

(The above signals at zero time represent the "zeroing" information, and are stored in memory to be in the real time density calculations.);

$I_{1c1}$ is the radiant signal at measurement time, measured through the cuvette at wavelength $\lambda_1$;

$I_{0r1}$ is the radiant signal, at measurement time, measured through the reference path, at wavelength $\lambda_1$;

$I_{1c2}$ is the radiant signal at measurement time, measured through the cuvette at wavelength $\lambda_2$;

$I_{1r2}$ is the radiant signal at measurement time, measured through the reference path, at wavelength $\lambda_2$;

$I_{1D}$ is the signal at measurement time, with the light source off;

(The above signals represent the real time information).

Figure 5:
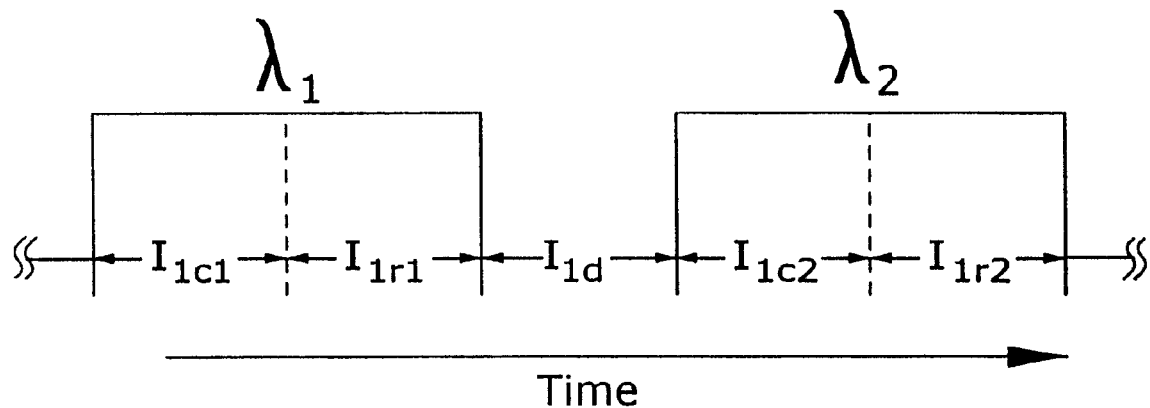
FIG. 5 is a diagram illustrating the data acquisition and processing functions of the embodiment of FIG. 2.

The radiant signals above are taken for every discrete real time measurement of density, in the time sequence described in FIG. 5.

Ozone density is computed utilizing the following equations:

$$c = \frac{1}{\varepsilon L} \ln\left(\frac{\bar{I}_{0cl}}{I_{1cl}}\right)$$

$$\bar{I}_{0cl} = I_{0cl}\left(\frac{I_{1rl}}{I_{0rl}}\right)\left(\frac{I_{1c2}}{I_{0c2}}\right)\left(\frac{I_{0r2}}{I_{1r2}}\right)$$

where ($I_{1r2}/I_{0r1}$) represents the compensation for the variability relative to time zero of the source-detector pair at $\lambda_1$.

($I_{1r2}/I_{0r2}$) represents the compensation for the variability relative to time zero of the source-detector pair at $\lambda_2$.

($I_{1c2}/I_{0c2}$) represents the compensation for the variability of the optical properties of the cuvette relative to time zero.

Figure 2:
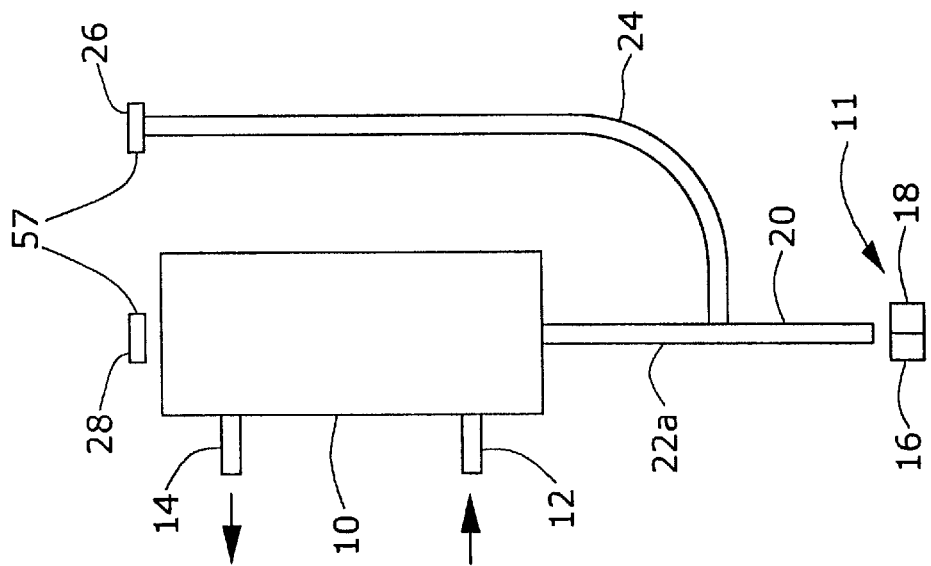
FIG. 2 depicts a dual wavelength measurement apparatus in accordance with one embodiment of the invention.

FIG. 2 illustrates an alternate embodiment comprising flow-through cell 10 having a gas inlet port 12 and a gas outlet port 14. A light source 11 comprising light emitting devices 16 and 18 is coupled to an optical light guide 20 which has one branch 22a coupled to the optical input end of cuvette 10, and having a second branch 24 coupled to a reference sensor 26, photosensors 26 and 28 comprising sensor apparatus 57. The optical output end of cell 10 has a measurement photosensor 28 disposed to receive light emanating from the output end of the cell 10. (Switching to provide alternating light output of sources 16 and 18 may be provided by processor 30 instructions to light source control 33.) The path through cell 10 serves as a measurement path, and the path to sensor 26 serves as a reference path. The light guides are installed to insure that their transmission properties will not change over time due to mechanical stress, thermal stress or other factors. The light emitting devices 16 and 18 may be, e.g., light emitting diodes (LEDs).

Figure 3:
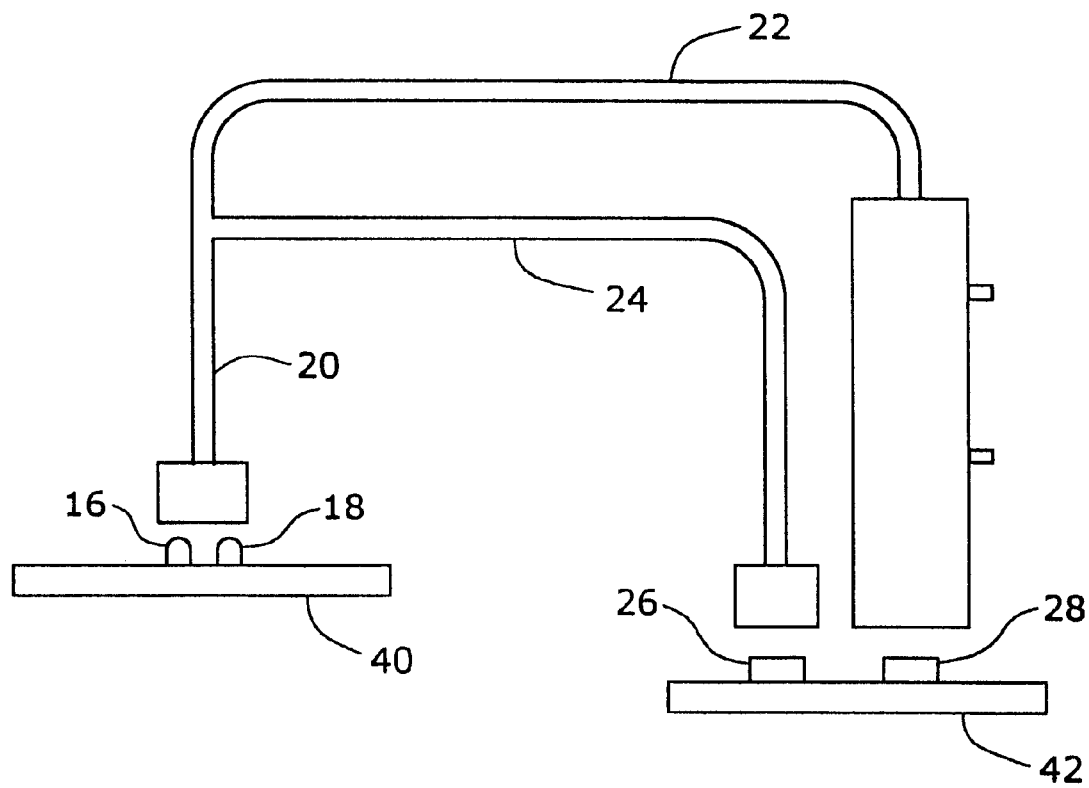
FIG. 3 depicts an embodiment of the apparatus of the invention showing the mounting of light sources and sensor pairs on respective substrates.
Figure 4:
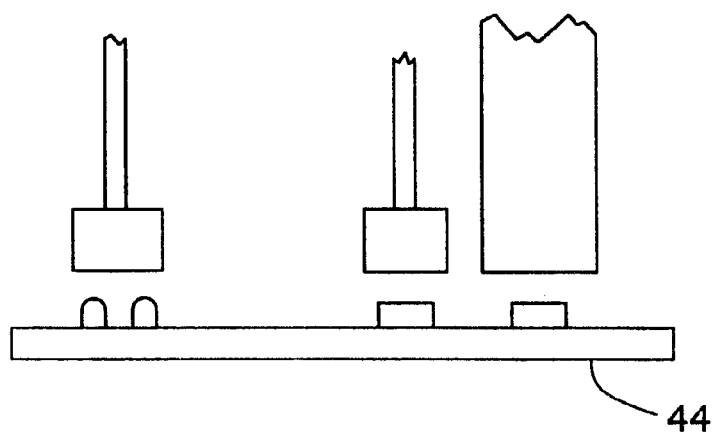
FIG. 4 is a cutaway view of an embodiment illustrating a single substrate on which the light sources and sensors are mounted.

FIG. 3 illustrates an embodiment in which light sources 16 and 18 are disposed on a common substrate 40 and coupled to light guide 20. Photosensors 26 and 28 are mounted on a common substrate 42. The substrates 40 and 42 may alternatively be a common substrate, i.e., single substrate 44, as shown in FIG. 4. The substrate may also contain the associated circuitry to simplify the packaging of the apparatus.

When the instrument is in operation, light source 11 alternately switches light emitting devices 16 and 18, having light output at wavelengths corresponding to $\lambda_{max}$ and $\lambda_{min}$ in the visible spectrum, on and off so as to transmit light to photosensors 26 and 28 through the light guides 22 and 24. As seen in the figures, the alternating light output is simultaneously directed to sensors 26 and 28, light output to sensor 28 being directed through cuvette 10 and the gas sample therein. The light from the devices 16 and 18 is also directed to reference sensor 26, and it is seen that the light along the reference path does not pass through the gas sample in cuvette 10. The photosensors 26 and 28 provide signals representative of the intensity of light received by the sensors. Since each sensor receives light from both devices 16 and 18, compensation is provided by the associated circuitry for differential drift which may occur in the intensity of the two light sources.

The output of light devices 16 and 18 corresponds to the visible wavelength-maxima and minima for the gas being measured. For example, in the case of ozone, the visible maximum is about 604 nm (i.e., in the Chappuis band) and the minima is about 850 nm ($\lambda_1$ and $\lambda_2$, respectively.)

Figure 6:
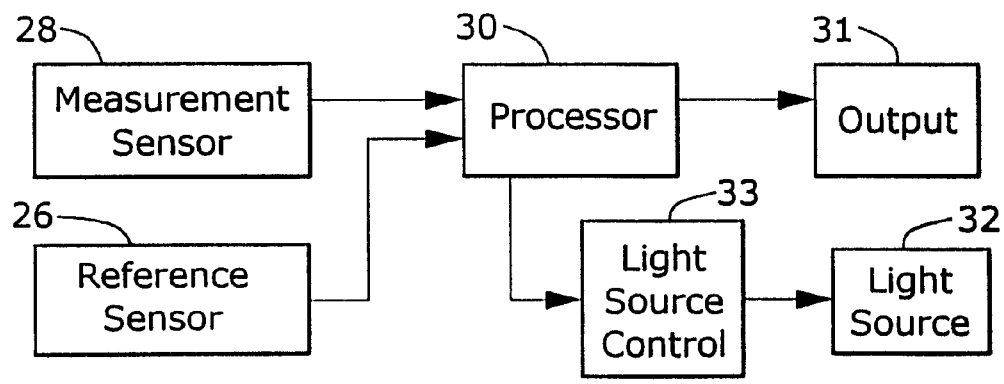
FIG. 6 is a diagram illustrating the data acquisition and processing functions of the embodiment of FIGS. 1 and 3.

A typical mode of operation of these embodiments is described as follows, with further references to block diagram FIG. 6. The instrument is zeroed by insuring that the cuvette is clear of sample gas containing the gas of interest. Desirably, a reference gas is introduced into the system and reference intensity values at $\lambda_{max}$ and $\lambda_{min}$ are taken through the cell at measurement sensor 28, and at reference sensor 26. These values are provided to processor 30 for storage in memory as constants. Next, sample gas is introduced into cuvette 10, and the above procedure is repeated to obtain measurement of light intensity at both wavelengths through the sample and at the reference sensor. Two additional measurements are performed with light devices 16 and 18 turned off, to obtain a dark current value of the sensors 26 and 28. The dark current readings may be desirably used to offset the other readings and compensate for sensor and electronic noise.

The readings from memory taken in the above procedure are employed by processor 30 to calculate the concentration of the desired gas component as described above. The output from processor 30 representing the concentration of the desired gas component is provided to an output device 31 which may be a data recorder, data storage device or display. The processor 30 also provides control signals to light source control 33 which provides energizing signals to light source 32 which, in this embodiment, comprises sources 16 and 18.

Other embodiments and variations of the disclosed invention will be apparent to those of ordinary skill in the art without departing from the inventive concepts contained herein. Accordingly, this invention is to be viewed as embracing each and every novel feature and novel combination of features present in or possessed by the invention disclosed herein and is to be viewed as limited solely by the scope and spirit of the appended claims.

We claim:

1. A system for detection of ozone in a gas mixture, comprising:
   a. a light source providing light output in the visible spectrum at a first wavelength at which ozone has maximum absorption, and a second wavelength at which ozone has minimum absorption;
   b. a cell for containing a gas in which ozone is to be detected and through which the light output from said light source is transmitted;
   c. sensor apparatus for receiving the light output from said cell and directly from said light source and for providing electrical outputs representing the intensity of light received from the cell and directly from the light source;
   d. a processor for receiving the electrical outputs of the sensor apparatus and operative to calculate the concentration of ozone in the gas contained in the cell.

2. The system of claim 1 wherein the light source is switched to alternately provide the light output at the first wavelength and the second wavelength;
   and wherein the sensor apparatus is switched to alternately receive light from the cell and directly from the light source at the first and second wavelengths.

3. The system of claim 2 wherein the cell is a flow cell having a gas input and a gas output through which a gas sample is caused to flow.

4. The system of claim 3 wherein the light output from the light source is conveyed to the cell and to the sensor apparatus by light guides.

5. The system of claim 4 wherein the sensor apparatus includes first and second light sensors operative respectively to receive the light output from the cell and directly from the light source.

6. The system of claim 4 wherein the sensor apparatus includes a single light sensor operative to receive the light output from the cell and directly from the light source.

7. The system of claim 5 wherein the first and second light sensors are contained on a common substrate.

8. The system of claim 7 wherein the light source includes first and second light emitting devices providing respectively the light output at the first and second wavelengths.

9. The system of claim 8 wherein the first and second light emitting devices are contained on a common substrate.

10. The system of claim 9 wherein the common substrates are the same substrate.

11. The system of claim 1 wherein the processor is operative to calculate ozone concentration according to the Beer-Lambert formula.

12. The system of claim 2 wherein the light source provides the light output at the first and second wavelengths in alternating manner.

13. The system of claim 1 wherein the ozone to be detected in the gas mixture is at a concentration of at least about 300 g/Nm$^3$.

14. The system of claim 1 wherein the light output at the first wavelength is in the chappuis band.

15. The system of claim 5 wherein the light output at the first wavelength is about 604 nm and the light output at the second wavelength is about 850 nm.

16. A system for detection of a fluid/gas species, said species exhibiting absorption bands within a spectrum of radiation, comprising:

a. a light source providing multiple wavelength light output in said spectrum of radiation, wherein the light output at a first wavelength is about 604 nm and the light output at a second wavelength is about 850 nm;

b. a cell for containing a fluid/gas mixture in which said fluid/gas species is to be detected and through which the light output from said light source is transmitted;

c. sensor apparatus for receiving the light output from said cell and directly from said light source and for providing electrical outputs representing the intensity of light received from the cell and directly from the light source; and d. a processor for receiving the electrical outputs of the sensor apparatus and operative to calculate the concentration of said fluid/gas species contained in the cell.

* * * * *

UNITED STATES PATENT AND TRADEMARK OFFICE
CERTIFICATE OF CORRECTION

PATENT NO. : 6,010,665  
DATED : January 4, 2000  
INVENTOR(S) : Victor J. Dosoretz et al.

Page 1 of 1

It is certified that error appears in the above-identified patent and that said Letters Patent is hereby corrected as shown below:

Column 2,  
Line 56, "≈" should read -- ≅ --;

Column 4,  
Line 8, "18 for" should read -- 18 as seen in, e.g., Fig. 2, for --;  
Line 27, "signal," should read -- signal to zerotime, --;  
Line 36, "signals to zero time" should read -- signals represent the --;  
Line 37, "to be in" should read -- to be used in --;  
Line 64, "$(I_{1r2}/I_{0r1})$" should read -- $(I_{1r1}/I_{or1})$ --; and Column 7,  
Line 8, "chappuis" should read -- Chappuis --.

Signed and Sealed this

Twelfth Day of March, 2002

*Attest:*

*Attesting Officer*

JAMES E. ROGAN  
*Director of the United States Patent and Trademark Office*